United States Patent [19]

Hong

[11] Patent Number: 5,183,564

[45] Date of Patent: Feb. 2, 1993

[54] STIRRING DEVICE FOR FACILITATING DIALYSIS

[76] Inventor: Chin-Chen Hong, 8th Fl., No. 62-5, Hsi-Ning N. Rd., Taipei, Taiwan

[21] Appl. No.: 802,533

[22] Filed: Dec. 5, 1991

[51] Int. Cl.$^5$ ............................................. B01D 61/28
[52] U.S. Cl. ...................................... 210/232; 74/55; 74/109; 210/94; 210/138; 210/321.71; 366/208; 366/216; 422/101; 422/102; 422/104
[58] Field of Search ................. 210/138, 94, 148, 232, 210/319, 321.63, 321.71; 366/208, 216, 276; 74/55, 109; 422/101, 102, 104, 258

[56] References Cited

U.S. PATENT DOCUMENTS

| | | | |
|---|---|---|---|
| 3,623,611 | 11/1971 | Riley et al. | 210/321.84 |
| 3,882,735 | 5/1975 | Shimodaira et al. | 74/109 |
| 4,118,801 | 10/1978 | Kraft et al. | 366/208 |
| 4,258,580 | 3/1981 | Lowe | 74/109 |
| 4,747,693 | 5/1988 | Kahl | 422/104 |
| 5,059,393 | 10/1991 | Quenin et al. | 74/55 |

Primary Examiner—Robert A. Dawson
Assistant Examiner—Sun Uk Kim
Attorney, Agent, or Firm—Sughrue, Mion, Zinn, Macpeak and Seas

[57] ABSTRACT

A stirring device for facilitating dialysis includes a housing, an axle with a first end portion extending out of the housing and a second end portion extending into the housing, a sprocket connected to the second end portion of the axle, a motor unit provided inside the housing, a circular cam plate mounted eccentrically on and being rotatably driven by a driving shaft of the motor unit, and a cam follower having a curved edge provided with gear teeth which mesh with the sprocket. The cam follower is formed with a cam groove to receive the cam plate. Rotation of the cam plate inside the cam groove causes reciprocating left and right movement of the cam follower to bring about reciprocating clockwise and counterclockwise rotation of the sprocket and the axle. A dialysate chamber confines a receiving space to receive a volume of solvent. The dialysate chamber is provided on top of the housing and is formed with an axially extending tubular sleeve. A sample tube holder is provided inside the dialysate chamber and has a shaft portion that extends into the tubular sleeve. The shaft portion is connected to the first end portion of the axle and has an upper end provided with a tube support portion to hold analytical test tubes.

8 Claims, 4 Drawing Sheets

STIRRING DEVICE FOR FACILITATING DIALYSIS

BACKGROUND OF THE INVENTION

1. Field of the Invention

The invention relates to a stirring device, more particularly to a stirring device for facilitating dialysis.

2. Description of the Related Art

Dialyzers are used to separate ribonucleic acids, amino acids and proteins. FIG. 1 is an illustration of a conventional System 100 microdialyzer developed by Pierce. In the conventional microdialyzer, sample tubes are provided on a sample well plate (B). Linear stirring of the well plate (B) is then conducted so as to facilitate the diffusion of unwanted low-molecular weight particles into a dialysate chamber (C). The desired particles are then recovered from the sample tubes through the use of appropriate devices (such as pipettes). The main drawback of the conventional microdialyzer is that the required dialysis time is relatively long. Thus, significant losses in sample can occur unless the dialysis time can be greatly reduced.

SUMMARY OF THE INVENTION

Therefore, the main objective of the present invention is to provide a stirring device with a reciprocating rotating motion, which stirring device enhances the collision of particles inside the sample tubes so as to improve the diffusion of unwanted particles, thereby greatly reducing the dialysis time.

Another objective of the present invention is to provide a stirring device which is simple in construction and which is easy to operate.

Accordingly, the preferred embodiment of a stirring device of the present invention comprises:

a housing;

a mechanical driving assembly including: an axle having a first end portion extending out of the housing and a second end portion extending into the housing; a sprocket connected to the second end portion of the axle; a motor unit provided inside the housing and having a driving shaft; a circular cam plate mounted eccentrically on and being rotatably driven by the driving shaft; and a cam follower having a curved edge provided with gear teeth which mesh with the sprocket, said cam follower being formed with a cam groove to receive the cam plate, and rotation of the cam plate inside the cam groove causing reciprocating left and right movement of the cam follower to bring about reciprocating clockwise and counterclockwise rotation of the sprocket and the axle;

a dialysate chamber formed as a hollow cylinder that confines a receiving space to receive a volume of solvent, said dialysate chamber being provided on top of the housing and being formed with an axially extending tubular sleeve;

a sample tube holder provided inside the dialysate chamber and having a shaft portion that extends into the tubular sleeve of the dialysate chamber, said shaft portion being connected to the first end portion of the axle and having an upper end provided with a tube support portion that is formed with a plurality of angularly spaced tube receiving holes for holding analytical test tubes; and a control unit to control the speed and the operating time of the motor unit.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
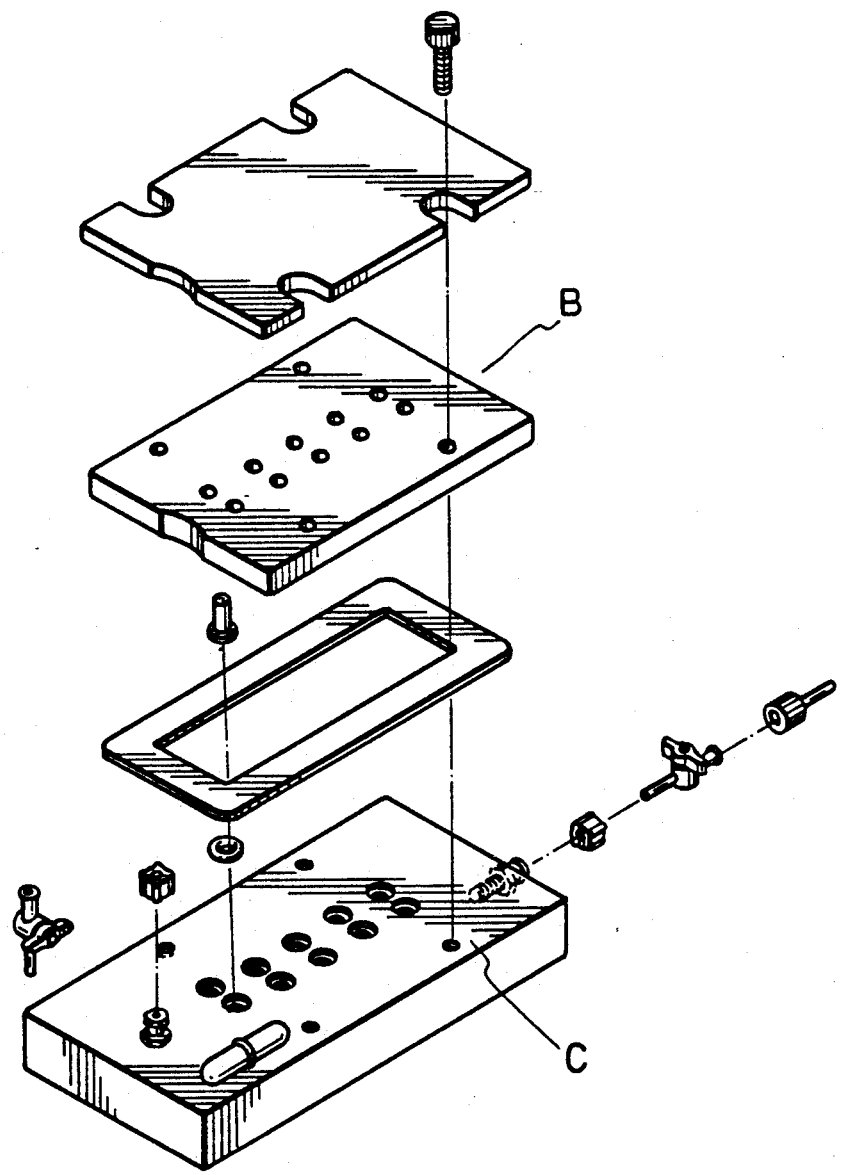
FIG. 1 is an exploded view of a conventional dialyzer.
Figure 2:
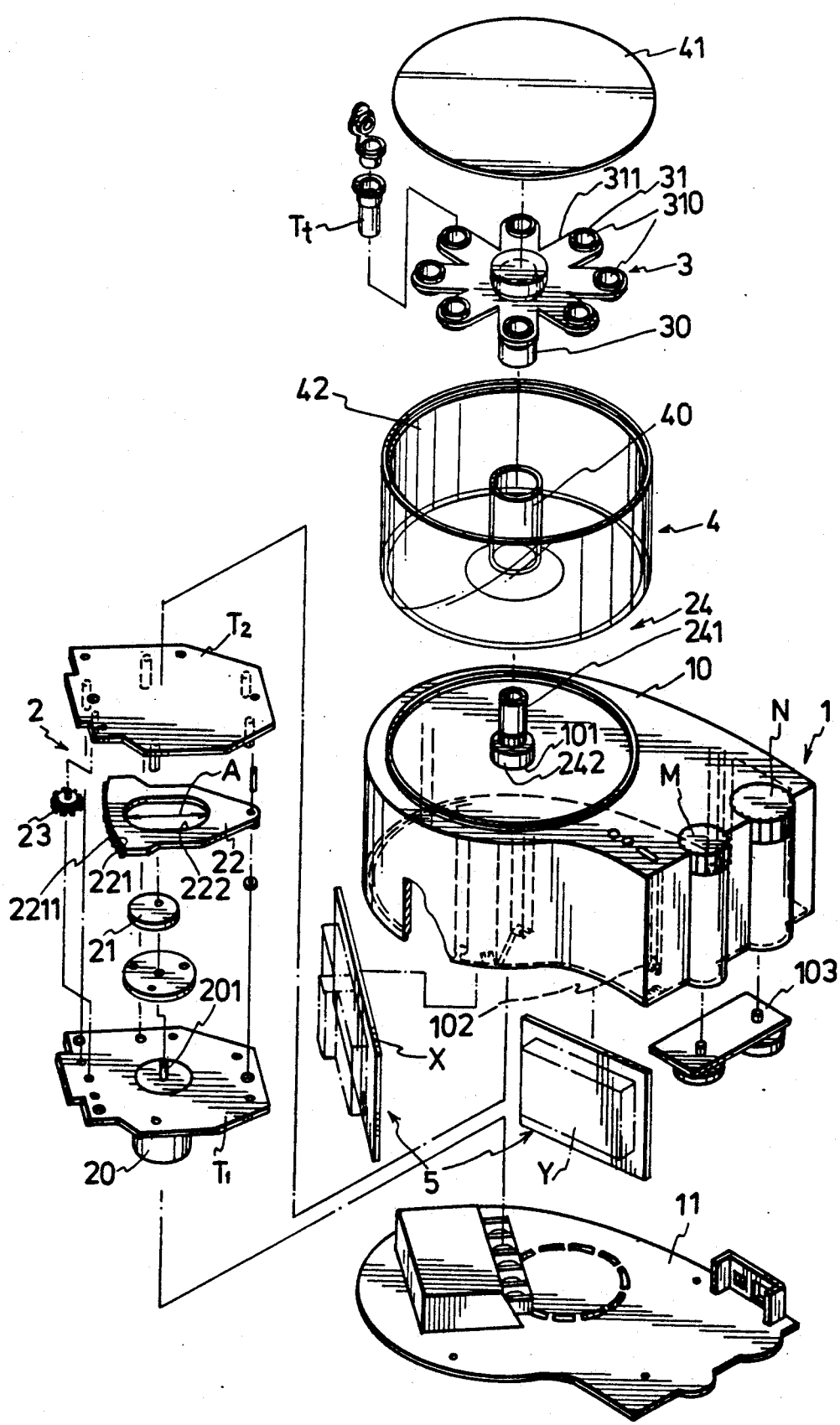
FIG. 2 is an exploded view of the preferred embodiment of a stirring device according to the present invention.
Figure 3:
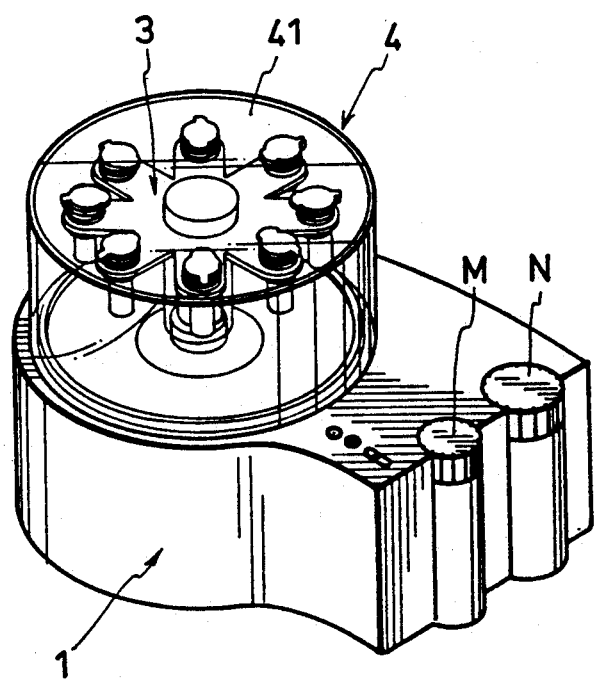
FIG. 3 is a perspective view of the preferred embodiment illustrating its assembly.

Referring to FIGS. 2 and 3, the preferred embodiment of a stirring device according to the present invention is shown to comprise a housing (1), a mechanical driving assembly (2), a sample tube holder (3), a dialysate chamber (4) and a control unit (5).

The housing (1) includes upper and lower housing parts (10, 11) which are mounted to one another through the use of screws (not shown). Each of the housing parts (10, 11) are provided with a rounded portion. The upper housing part (10) is formed with an axle opening (101) at the center of the rounded portion thereof. The inner surface of the upper housing part (10) is provided with two pairs of positioning rails (102) and a mounting seat (103) to hold the control unit (5) in place.

The mechanical driving assembly (2) includes a motor unit (20), a cam plate (21), a cam follower (22), a sprocket (23) and an axle (24). The axle (24) is to be provided on the axle opening (101) of the upper housing part (10). One end portion (241) of the axle (24) extends out of the housing (1) and is used to rotate the sample tube holder (3). The other end portion (242) of the axle (24) is connected to the sprocket (23). The cam plate (21) is a circular plate which is mounted eccentrically on a driving shaft (201) of the motor unit (20). The cam follower (22) is substantially sectoral in shape and has a curved edge (221) provided with gear teeth (2211) which mesh with the sprocket (23). The cam follower (22) is formed with a radially extending oblongated cam groove (222) to receive the cam plate (21). During actual assembly, the motor unit (20) and the cam plate (21) are provided on two sides of a first mounting plate (T1). The cam follower (22) has one end pivoted to a second mounting plate (T2). The second mounting plate (T2) is secured to the upper housing part (10). A plurality of pins are then provided so as to join the first and second mounting plates (T1, T2). This illustrates how the mechanical driving assembly (2) is provided inside the housing (1).

Referring once more to FIG. 2, the length of the major axis (A) of the cam groove (222) should be equal to twice the diameter of the cam plate (21). Rotation of the cam plate (21) inside the cam groove (222) causes reciprocating left and right movement of the cam follower (22), as will be detailed in the succeeding paragraphs. Reciprocating left and right movement of the cam follower (22) can cause reciprocating 180° clockwise and counterclockwise rotation of the sprocket (23) and the axle (24).

The sample tube holder (3) has a tubular shaft (30) to be sleeved on the end portion (241) of the axle (24). The tubular shaft (30) has a toothed internal portion (not shown) which engages a toothed external portion of the axle (24), thus preventing rotation of the sample tube holder (3) relative to the axle (24). A tube support portion (31) is provided on an upper end of the shaft (30) and includes a plurality of radially extending and angularly spaced arms (311). Each of the arms (311) has a distal end provided with a tube receiving hole (310) for holding an analytical test tube (Tt).

The dialysate chamber (4) is a hollow transparent cylinder provided on top of the housing (1). The dialysate chamber (4) confines a receiving space (42) sufficient to enclose the sample tube holder (3). The shaft (30) of the sample tube holder (3) extends into a tubular sleeve (40) of the chamber (4). The upper end of the shaft (30) can block the tubular sleeve (40) when the sample tube holder (3) is mounted onto the dialysate chamber (4). A cover plate (41) is detachably provided on an open top end of the dialysate chamber (4) so as to access the receiving space (42).

The control unit (5) is provided to control the supply of electric power to the motor unit (20). The control unit (5) includes a motor speed control circuit and a motor operating time control circuit. Such control circuits are known to one skilled in the art and will not be detailed herein. The circuit components of the control unit (5) are mounted onto a pair of circuit boards (X, Y). The circuit boards (X, Y) are mounted inside the upper housing part (10) via the positioning rails (102). The circuit components are also connected to a pair of control knobs (M, N) secured to the mounting seat (103).

Figure 4:
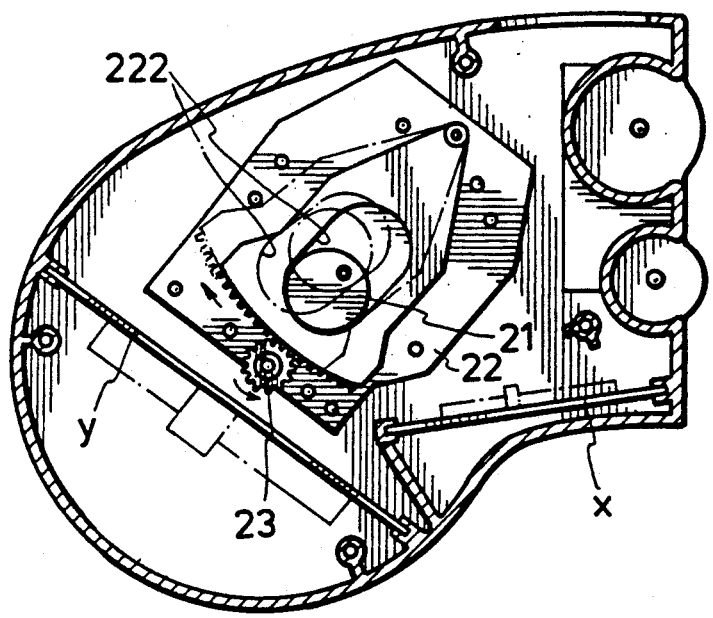
FIGS. 4 and 5 illustrate the movement of a mechanical driving assembly of the stirring device of the present invention.
Figure 5:
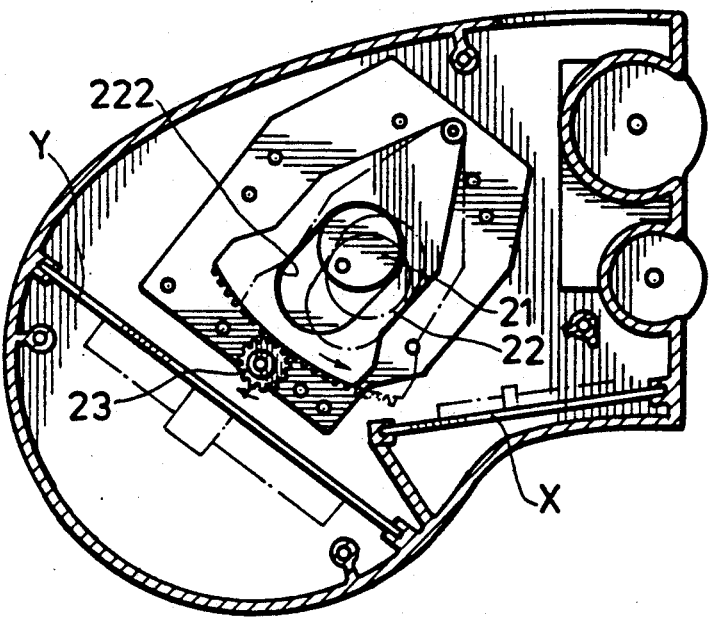

The movement of the mechanical driving assembly (2) is shown in FIGS. 4 and 5. Referring to FIG. 4, when the cam plate (21) is rotated so as to move from a first dead point to a second dead point on the cam groove (222), the cam plate (21) urges the cam follower (22) to pivot to the left side, thereby causing the sprocket (23) to rotate in a counterclockwise direction. Referring to FIG. 5, when the cam plate (21) is further rotated so as to move from the second dead point to the first dead point on the cam groove (222), the cam plate (21) urges the cam follower (22) to pivot to the right side, thereby causing the sprocket (23) to rotate in a clockwise direction. Reciprocating clockwise and counterclockwise rotation of the sprocket (23) is therefore produced if the cam plate (21) is continuously rotated.

When using the preferred embodiment in a dialysis process, the sample which is to be processed is first poured into an analytical test tube (Tt). The test tube (Tt) is then mounted on one of the tube receiving holes (310) of the sample tube holder (3). A volume of solvent (such as distilled water) is poured in the dialysate chamber (4). The motor unit (20) is then activated so as to cause reciprocating left and right movement of the cam follower (22) and thereby produce reciprocating clockwise and counterclockwise movement of the sprocket (23) and the axle (24). The sample tube holder (3) rotates with the axle (24), thus facilitating the diffusion of low-molecular weight solutes of the sample through the analytical test tube (Tt) during the dialysis process.

The characterizing features and the advantages of using the preferred embodiment of a stirring device of the present invention are as follows:

1. The reciprocating clockwise and counterclockwise rotation of the sample tube holder (3) facilitates the diffusion of low-molecular weight solutes in the sample during a dialysis process.

2. The configuration of the cam plate (21) and the cam follower (22) permit reciprocating 180° clockwise and counterclockwise rotation of the sprocket (23).

3. The operation and the construction of the preferred embodiment has been simplified so as to permit faster and more effective isolation of high-molecular weight solute, which in turn can be used in recombinant DNA technology.

While the present invention has been described in connection with what is considered the most practical and preferred embodiment, it is understood that this invention is not limited to the disclosed embodiment, but is intended to cover various arrangements included within the spirit and scope of the broadest interpretation so as to encompass all such modifications and equivalent arrangements.

I claim:

1. A stirring device for facilitating dialysis, comprising:
   a housing;
   a mechanical driving assembly including: an axle having a first end portion extending out of said housing and a second end portion extending into said housing; a sprocket connected to said second end portion of said axle; a motor unit provided inside said housing and having a driving shaft; a circular cam plate mounted eccentrically on and being rotatably driven by said driving shaft; and a cam follower having a curved edge provided with gear teeth which mesh with said sprocket, said cam follower being formed with a cam groove to receive said cam plate, and rotation of said cam plate inside said cam groove causing reciprocating left and right movement of said cam follower to bring about reciprocating clockwise and counterclockwise rotation of said sprocket and said axle;
   a dialysate chamber formed as a hollow cylinder that confines a receiving space to receive a volume of solvent, said dialysate chamber being provided on top of said housing and being formed with an axially extending tubular sleeve; and
   a sample tube holder provided inside said dialysate chamber and having a shaft portion that extends into said tubular sleeve of said dialysate chamber, said shaft portion being connected to said first end portion of said axle and having an upper end provided with a tube support portion that is formed with a plurality of angularly spaced tube receiving holes for holding analytical test tubes.

2. The stirring device as claimed in claim 1, wherein said cam follower is substantially sectoral in shape, and said cam groove extends radially and is oblong in shape.

3. The stirring device as claimed in claim 2, wherein said cam groove has a major axis with a length that is twice the diameter of said cam plate.

4. The stirring device as claimed in claim 3, wherein reciprocating left and right movement of said cam follower brings about reciprocating 180° clockwise and counterclockwise rotation of said sprocket and said axle.

5. The stirring device as claimed in claim 1, wherein said tube support portion of said sample tube holder comprises a plurality of radially extending and angularly spaced arms, each of said tube receiving holes being formed on a distal end of a corresponding one of said arms.

6. The stirring device as claimed in claim 1, wherein said dialysate chamber is made of a transparent material.

7. The stirring device as claimed in claim 1, wherein said dialysate chamber has a cover plate detachably provided on an open top end thereof so as to access said receiving space.

8. The stirring device as claimed in claim 1, further comprising a control unit to control the speed and the operating time of said motor unit.

* * * * *